(12) United States Patent
Mougin et al.

(10) Patent No.: US 6,495,374 B1
(45) Date of Patent: Dec. 17, 2002

(54) FLUID SAMPLING DEVICE COMPRISING A THERMAL CONTROL VALVE

(75) Inventors: Pascal Mougin, Rueil-Malmaison (FR); Philippe Ungerer, Créret (FR); Gérard Moracchini, Hameau Margency (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/382,327

(22) Filed: Aug. 24, 1999

Related U.S. Application Data

(62) Division of application No. 09/094,634, filed on Jun. 15, 1998, now Pat. No. 5,997,819.

(30) Foreign Application Priority Data

Jun. 17, 1997 (FR) .............................. 97 07610

(51) Int. Cl.[7] .................................. G01N 1/10
(52) U.S. Cl. ........................ 436/180; 436/174; 422/100; 422/103; 73/863.12; 137/251.1
(58) Field of Search .......................... 422/99, 100, 103; 436/174, 179, 180; 73/1.04, 863.12, 864.01; 137/251.1, 828, 13

(56) References Cited

U.S. PATENT DOCUMENTS

| | | | |
|---|---|---|---|
| 3,429,186 A | 2/1969 | Price et al. ................ | 73/421.5 |
| 4,259,867 A | 4/1981 | Fondos et al. ............. | 73/421.5 |
| 4,367,645 A | 1/1983 | Froment ..................... | 73/23.1 |
| 4,576,918 A | 3/1986 | Yeung ........................ | 436/179 |
| 5,101,848 A | * 4/1992 | Kojima et al. ................ | 137/13 |
| 5,125,427 A | * 6/1992 | Cantu et al. .................. | 137/13 |
| 5,795,788 A | * 8/1998 | Bevan et al. ............... | 436/161 |
| 5,855,852 A | * 1/1999 | Bienhaus et al. ........... | 422/102 |
| 5,879,635 A | * 3/1999 | Nason ........................ | 422/102 |
| 5,988,197 A | * 11/1999 | Colin et al. .................... | 137/13 |

FOREIGN PATENT DOCUMENTS

| | | |
|---|---|---|
| DE | 3423200 | 1/1985 |
| DE | 3528924 | 10/1988 |
| GB | 2326477 A | * 12/1998 |

* cited by examiner

*Primary Examiner*—Jill Warden
*Assistant Examiner*—Kathryn Bex
(74) *Attorney, Agent, or Firm*—Antonelli, Terry, Stout & Kraus, LLP

(57) ABSTRACT

Fluid sampling device comprising a sampling cell (1) provided with a thermal control valve having a plug (21) made from a solid low-melting temperature material that is made permeable to the fluid by temporary heating. The device comprises an intermediate cell (6) with a central channel (7) provided with a plug made from the solid material, which communicates an inlet with a first end and an outlet with the opposite end, and suited to tightly fit into the inlet hole of the sampling cell, a device (12, 13) for connecting the two cells (1, 6) to each other and an element (14) associated with a seal (20) for connecting, at the inlet of intermediate cell (6), a linking tube (15) to a reactor (17) producing the fluid to be sampled.

6 Claims, 2 Drawing Sheets

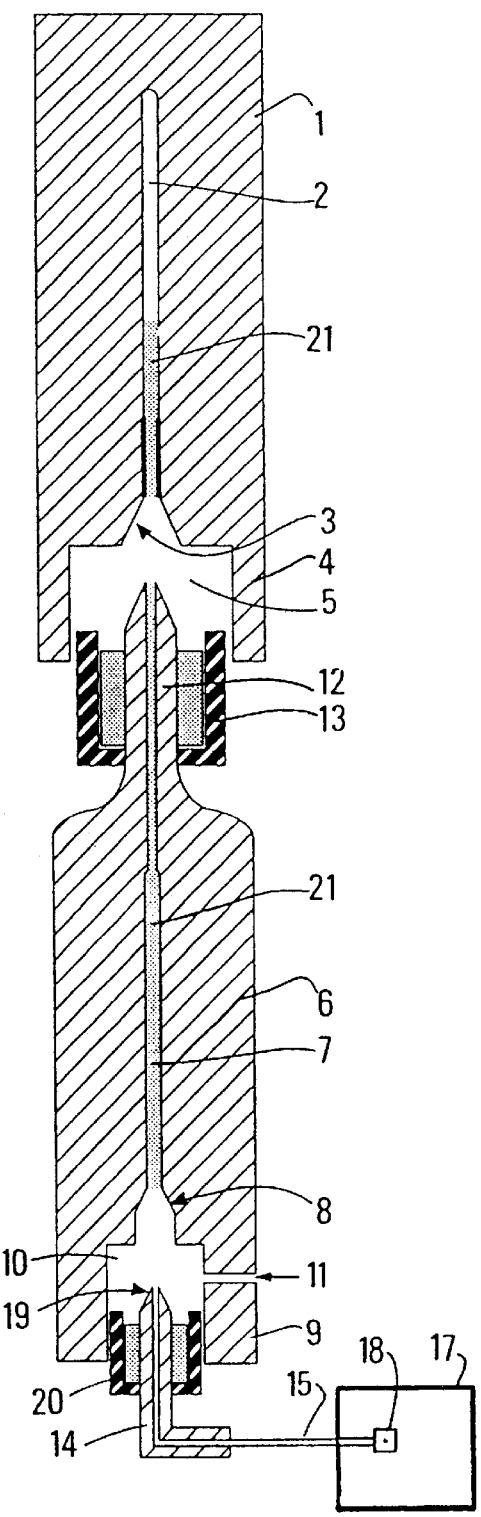
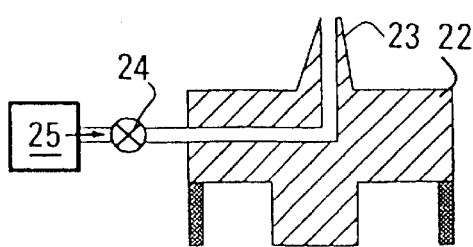
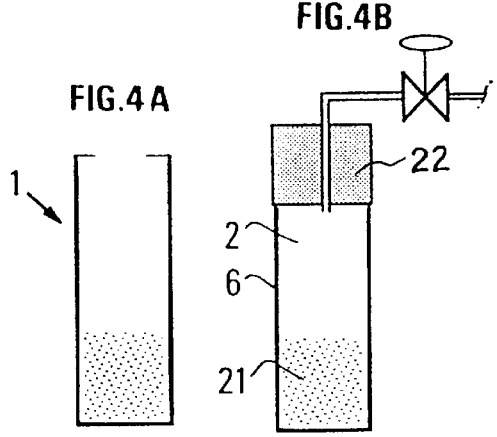
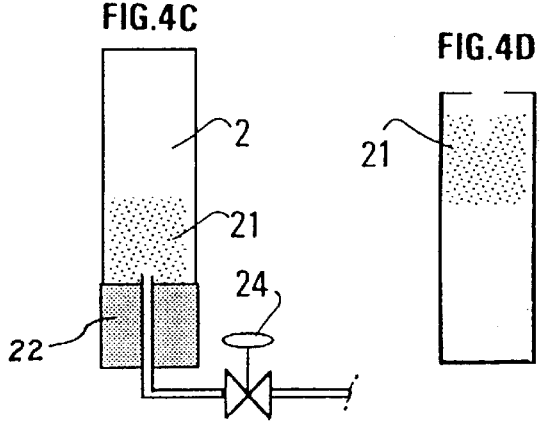

FIG.2

| Nom | % Sn | % Bi | % Pb | % Cd | Divers | Tf (°C) |
|---|---|---|---|---|---|---|
|  | 99.25 |  |  |  | 0.5 % Cu | 227 |
|  | 25.9 | 53.9 |  | 20.2 |  | 103 |
| Wood | 12.5 | 50 | 25 | 12.5 |  | 70 |
| Cerrolow | 8.3 | 44.7 | 22.6 | 5.3 | 19.1 % In | 47 |

FLUID SAMPLING DEVICE COMPRISING A THERMAL CONTROL VALVE

This application is a divisional application of U.S. Ser. No. 09/094,634, filed Jun. 15, 1998 now U.S. Pat. No. 5,997,819.

BACKGROUND OF THE INVENTION

1. Field of the Invention

The present invention relates to a fluid sampling device comprising a thermal control valve.

2. Description of the Prior Art

Two prior art methods are known.

The first approach, is described for example by:

Ungerer P. et al, 1988, in Kinetic Modelling of Oil Cracking, Org. Geochem., 13,857–868, carries out pyrolyses of increasing duration. At the end of each of the successive experiments, the kinetics are stopped by means of an abrupt temperature drop. The conversion coefficients and the reaction rates are thus acquired at different times.

The second approach performs successive samplings during the progress of a single experiment. Considering the duration, of pyrolysis reactions, this approach has the advantage of reducing the total acquisition time. The entire kinetics can be obtained with a single handling whereas the number of experiments should be multiplied with the first technique. The method of operation through sampling also allows a determination that the reactive medium has always had the same (thermal and therefore reaction) history in time, which is not always the case when experiments are repeated. On the other hand, using successive samplings requires a greater reaction volume in order to make sure that the sum of the various aliquots extracted in the course of time will not lead to considerable changes in the operating conditions of the reaction system. The implementation difficulty of this approach at high pressures is due to the considerable dead volume inherent in conventional needle valves.

SUMMARY OF THE INVENTION

The fluid sampling device according to the invention, which comprises a sampling cell for collecting fluid, provided with an inlet hole, is characterized in that the sampling cell is insulated by a thermal control valve consisting of a plug made from a solid low-melting temperature material that is made permeable to the fluid by temporary heating.

The device of the invention lends itself to many applications where control of an evolutionary process or characterization of phase equilibria requires successive and distinct fluid samplings while reducing the effects of contamination due to dead volumes remaining in the sampling circuits.

The sampling device according to the invention can be used for example to take fluid samples within the scope of oil or fluid pyrolyses in closed reactors. In order to be representative of the evolution of natural basins, these reactions last for several days or even several weeks. The kinetics of such reactions can be obtained according to two approaches.

According to a preferred embodiment, the plug that seals the inlet hole is made from a stable melting temperature eutectic metal alloy such as Wood's metal for example.

According to an embodiment, the device of the invention comprises an intermediate cell with a central channel provided with a plug made of the solid material, which communicates with an inlet with a first end and an outlet with the opposite end thereof, and is suited to tightly fit into the inlet hole of the sampling cell, a connection for connecting the sampling cell to the intermediate cell, an element associated with a seal for connecting, at the inlet of the intermediate cell, a fine linking tube to a reactor producing the fluid to be sampled.

According to an embodiment suited for fluid sampling under elevated pressure, the sampling cell is provided with a fine inlet channel, the section and the length of this inlet channel and those of the central channel of the intermediate cell are so selected that the plugs formed by cooling of the material are sealed against the fluid sampled.

The method for implementing the device according to the invention comprises: a sampling cell preparation step comprising transfer of a certain volume of the material in the liquid state into the cell, suction of the fluid contained in the cell, transfer of the volume of material into the inlet of the cell and cooling thereof so as to form a sealed plug; and a sampling step comprising communicating the sampling cell with a vessel containing the fluid to be sampled, and temporary heating of the plug (which leads to the melting thereof) in order to make it permeable to the fluid.

According to an embodiment, the method further comprises a step of preparation of an intermediate cell in order to form therein a second solid plug made from the material, the sampling also comprising combined heating of the second plug in order to make it permeable to the fluid.

A capillary tube is preferably used to connect the reactor to the intermediate cell so as to minimize dead volumes.

Fluid ampoules are thus available for subsequent treatments. There is no constraint concerning the conservation thereof and this storage method allows high flexibility during later analyses. The consequence of certain sampling methods is the use of suited analysis techniques: in many fluid analysis cases, specific chromatography injectors have to be used. The sampling mode described hereafter requires no adjustment of existing sensing devices and all of the conventional devices can be used.

A valve of this type has many advantages in comparison with conventional valves used in laboratory devices:

The valve is economical while providing perfect sealing. The installation thereof is much simpler than that of a conventional valve. The installation simplicity thereof, combined with its low cost, makes it possible to manufacture sample ampoules that can optionally be expandable. A batch of ampoules containing fluid samples representative of successive times of a reaction spread over a relatively long period can be readily constituted and it is therefore possible to simplify the organization of the step of acquisition and processing of data relative to this reaction, which can last for a shorter time.

The characteristics of this type of valve are well reproducible, which facilitates comparisons between the successive fluid samples. It is also possible with this type of valve to reduce dead volumes to very little so that trails are negligible and the successive samples are entirely independent of one another.

Once the sampling is performed, the sampling cell can be removed, the intermediate cell with its solidified "thermal valve" tightly insulates the reaction chamber, and a new fluid recovery cell can be set for a new sampling operation.

BRIEF DESCRIPTION OF THE DRAWINGS

Other features and advantages of the method according to the invention will be clear from reading the description hereafter of a non limitative example suited to the sampling of fluid samples under very elevated pressure, with reference to the accompanying drawings wherein:

FIG. 1 diagrammatically shows the device with its various parts in a semi-dislodged position, FIG. 2 is a table of various alloys, with their composition and their melting temperature, which can be used to form the thermal-effect valve used in the present, device, FIG. 3 shows an end plug used in the preparatory stage prior to sampling, and FIGS. 4a, 4b, 4c, 4d illustrate various operations required for preparation of a sampling cell.

DETAILED DESCRIPTION OF THE PREFERRED EMBODIMENTS OF THE INVENTION

Sampling cell 1 comprises (FIG. 1) a fine central inlet channel 2 ending in a wide-necked end 3 and a tubular extension 4 whose section is larger than that of central channel 2, which forms an inlet cavity 5.

Each fluid sample is taken by means of an intermediate cell 6 through which a fine longitudinal channel 7 runs. At a first end, a fine channel 7 opens, through a wide-necked end 8, into a tubular extension 9 which forms an inlet cavity 10. A leakage hole 11 is radially provided through the wall of tubular extension 9. At the opposite end, intermediate cell 6 is extended by a beveled beak 12 suited to closely fit, during operation, into the wide-necked end 3 of sampling cell 1 so as to establish a continuity between the channels 2 and 7 of cells 1 and 6. An annular seal connection 13 whose section is suited to that of inlet cavity 5 of sampling cell 1 is associated with a pointed end 12.

The fluid to be transferred into intermediate cell 6 flows in through a joining element 14 in which a (0.2-mm inside diameter for example) capillary tube 15 connected to a high-pressure vessel (or cell) 17 containing the fluid to be sampled is inserted. A filter 18 made of sintered metal for example is placed at the inlet of the capillary tube (in high-vessel 17 for example) in order to hold back solid particles likely to be mixed with the fluid to be sampled. The other end of joining piece 14 ends in a point 19 suited to closely fit, during operation, into wide-necked end 8. An annular coupling 20 allows providing a sealed connection between joining piece 14 and inlet cavity 10.

Closing of the fine channels 2 and 7 in cells 1 and 6 is provided by "thermal-effect valves", in this case plugs 21 made from a low-melting point substance whose characteristics are suited to the application required.

In the case of applications where gaseous samples are to be taken at very high pressures that may reach 100 MPa, a low-melting point metal in the solid form is preferably used to form these sealed "thermal locks" between the reactive medium (high-pressure vessel 17) and the sampling zone (cells 1 and 6). During sampling, the solid metal is brought to the melting point thereof and the reactive fluid can then flow through the column of liquid metal and migrate to the sampling zone (sampling cell 1). Once the sample is obtained, the metal is cooled, it solidifies and thus entraps the fluid.

The metal used in the device must have a sufficiently low melting point so that it can be melted quite rapidly. The liquid-solid change must occur at a given temperature. It is thus possible to use a pure substance or alloys, but the latter must have a eutectic structure.

As shown in FIG. 2, various types of eutectic alloys based on tin, bismuth, lead and cadmium can be selected, with different melting temperatures according to the proportions of the various metal constituents.

According to the temperature of the reaction medium and of the environment of the sampling system, it is advisable to take the highest possible temperature compatible with the sample stability, thus preventing accidental melting of the metal. For standard temperature applications, the metal known as Wood's metal, which is an alloy of bismuth, lead, tin and cadmium and which has a melting point of 70° C., is for example used.

One of the main interests of these alloys is that they expand as they cool down, especially in the case of high bismuth contents. In general, when the bismuth content is above 55%, the alloys expand, and if this content falls below 48%, they shrink. There is almost no volume variation between these two values. This is notably the case with Wood's metal whose volume remains stable as it cools down, which prevents any possibility of leakage of the fluid entrapped in the sampling cell.

The wall of cells 1 and 6 is of course more or less thick according to the pressure of the samples taken, and the volume thereof is also suited to that of the samples to be taken.

The assembly described above forms the sampling device. The implementation thereof also requires various plugs which will serve for introduction of the alloy and possibly in case of a fluid leakage. All of these blocking elements comprise (FIG. 3) a first plug 22 suited to the inlet cavity 5 of the sampling cell, also provided with a pointed end 23 intended to come into contact with the bottom of wide-necked part 3. The plug is traversed by a bent channel opening into the point of pointed end 23, allowing to communication with the central channel 2 of sampling cell 1 with an evacuating device 25 by means of a valve 24 as explained hereunder.

Preparation of the Sampling Device

A preparation of cells 1 and 6 is performed prior to the sampling operations.

The opening at the end of pointed end 12 at one end of intermediate cell 6 is closed and the central channel (as shown in FIG. 2) is filled with metal brought to the melting point thereof. Rather slow cooling allows a high-grade metallic plug to form while avoiding mechanical stresses.

The sampling cell is prepared as follows. The opening thereof being directed upwards, a volume of liquefied metal is poured therein while hot (FIG. 4a) and it accumulates on the bottom. The cell opening is thereafter covered with the plug 22 of FIG. 4b and it is communicated through the opening of valve 24 with a water pump (not shown) so as to evacuate it (FIG. 4b). Valve 24 being closed, cell 1 is turned upside down and the entire cell is brought to the melting temperature so that the metal accumulates at the base (FIG. 4c). The metal 21 thereafter just has to be cooled to solidify and the sampling cell is thus sealed after plug 22 has been removed (FIG. 4d).

Assembly of the Device

The device is assembled as follows:

a) capillary tube 15 is first connected to reaction cell 17,
b) bent pipe 14 associated with coupling 20 is fitted into housing 8, 10 at the base of intermediate cell 6 so as to establish a continuity between beveled point 19 and central channel 7 closed by metallic plug 21, and
c) upper pointed end 12 and its associated connection 13 are similarly fitted into housing 3, 5 also in order to establish a continuity between the metallic plugs of cells 1,6.

Sampling

It is performed as follows:

Intermediate cell 6 and sampling cell 1 are brought to the melting temperature. The metal melts in channels 2 and 7, which makes it permeable to the fluid under pressure from high-pressure vessel 17. The fluid rises through the column of liquefied metal and accumulates in the sampling cell.

When sampling is completed, the metal is progressively cooled from the end of capillary tube 15 that is the closest to high-pressure vessel 17 up to sampling cell 1 so that the metallic plug which forms again is perfectly sealed.

Connection 13 then just has to be dismantled and the metallic bond that may have formed just has to be broken to release sampling cell 1. High-pressure vessel 17 is insulated by the cooled "thermal valve" of intermediate cell 6. The reaction kinetics can be stopped by quenching.

A new sampling cell 1 can then be coupled to intermediate cell 6 in order to perform a new sampling operation.

Using a capillary tube 15 allows reduction of the sampling volume. No draining is performed, the fluid present in the capillary tube, which has a thermal history that is different from that of the fluid in the reactor, is recovered but the volume thereof is negligible in relation to the sampled volume.

Sampling Device Dimensioning Methodology

Dimensioning of the device requires defining the minimum diameter of the tubes that are to be filled with metal. The required height of the metal plug which serves as a seal for the system under the pressure considered also has to be determined.

Preliminary experiments with variable diameter tubes must therefore be carried out in order to determine the minimum diameter so as to ensure passage of the fluid through columns of molten metal of different diameters because, if the diameter is too small, the capillary forces prevent ascent of the fluid drops or bubbles.

Once the diameter is selected, the height of metal required for the maximum pressure of the reactor has to be determined. This parameter can be estimated by means of numerical mechanical resistance simulations and checked by means of tests.

Variants

Without departing from the scope of the invention, it is also possible to use, for other applications where the pressures are much lower, a thermal valve using other materials than the alloys mentioned by way of example, or a sampling cell of any shape with a differently dimensioned inlet that can receive fluid samples without requiring an intermediate cell.

What is claimed is:

1. A method of sampling a fluid in a sampling cell provided with an inlet comprising:

a) connecting the sampling cell to a pump which pumps the cell to be void of any fluid and closing the inlet thereof by solidifying a thermal control valve comprising a plug made from a solid material, different from the fluid, with the solid material having a melting temperature, the plug being made permeable to the fluid by heating the plug to the melting temperature;

b) coupling the sampling cell with a vessel which provides the fluid to be sampled;

c) melting the plug by heating the plug to the melting temperature;

d) transferring the fluid sample through the melted plug into the sampling cell; and e) filling the sampling cell and cooling the melted plug to seal the fluid in the sampling cell; and wherein the thermal control valve is disposed between the sampling cell and the vessel when the melted plug is cooled to seal the fluid in the sampling cell.

2. A method as claimed in claim 1, comprising:

using an intermediate cell with an inlet and an outlet with a channel therebetween containing a plug of the solid material and connecting the inlet and the outlet of the intermediate cell respectively to the vessel and the inlet of the sampling cell;

heating the plugs of the sampling cell and the intermediate cell the melting temperature thereof to let a fluid sample pass through the melted plugs; and after hardening the plugs by cooling, disconnecting the intermediate cell from the sampling cell.

3. A method as claimed in claim 2, comprising:

connecting the vessel to the intermediate cell through a capillary tube in order to minimize dead volume.

4. A method as claimed in claim 1, comprising:

using a eutectic metal alloy as the solid material as a plug.

5. A method as claimed in claim 1, comprising:

using a Wood's metal as the plug.

6. A method for sampling a fluid in a sampling cell provided with an inlet and initially containing a gas, comprising:

preparing the sampling cell by heating a volume of a solid material, different from the fluid, to a melting temperature thereof, the solid material being permeable to the fluid to be sampled when heated to the melting temperature, forming in the sampling cell a solid plug by cooling the volume of melted material, evacuating the gas inside the sampling cell, turning upside down the sampling cell and heating the plug to the melting temperature thereof to transfer the plug into the inlet of the sampling cell, and cooling the plug to seal the sampling cell; and coupling the sampling cell with a vessel which provides fluid to be sampled, heating the sealing plug to a melting temperature thereof to melt the plug, passing the fluid sample through the melted sealing plug into the sampling cell, and hardening the plug by cooling the material.

* * * * *